(12) United States Patent
Davidson

(10) Patent No.: US 7,486,981 B2
(45) Date of Patent: Feb. 3, 2009

(54) SYSTEM AND METHOD FOR DISPLAYING AN IMAGE STREAM

(75) Inventor: Tal Davidson, Yoqneam Illit (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 10/986,918

(22) Filed: Nov. 15, 2004

(65) Prior Publication Data

US 2006/0106318 A1    May 18, 2006

(51) Int. Cl.
*A61B 5/05* (2006.01)
(52) U.S. Cl. .................. 600/407; 600/476; 324/306; 324/318
(58) Field of Classification Search ............... 600/407, 600/408; 324/306, 318
See application file for complete search history.

(56) References Cited

U.S. PATENT DOCUMENTS

| | | | |
|---|---|---|---|
| 4,243,652 A | 1/1981 | Francis | |
| 4,278,077 A | 7/1981 | Mizumoto | |
| 5,381,784 A | 1/1995 | Adair | |
| 5,603,687 A | 2/1997 | Hori et al. | |
| 5,604,531 A * | 2/1997 | Iddan et al. | 348/76 |
| 5,993,378 A | 11/1999 | Lemelson | |
| 6,173,317 B1 | 1/2001 | Chaddha et al. | |
| 6,208,354 B1 | 3/2001 | Porter | |
| 6,240,312 B1 | 5/2001 | Alfano et al. | |
| 6,504,990 B1 | 1/2003 | Abecassis | |
| 6,904,308 B2 | 6/2005 | Frisch et al. | |
| 6,976,229 B1 | 12/2005 | Balabanovic et al. | |
| 2001/0035902 A1 | 11/2001 | Iddan et al. | |
| 2002/0103417 A1 | 8/2002 | Gazdzinski | |
| 2002/0109774 A1 | 8/2002 | Meron et al. | |
| 2002/0177779 A1 | 11/2002 | Adler et al. | |
| 2003/0174208 A1 | 9/2003 | Glukhovsky et al. | |
| 2004/0027500 A1 | 2/2004 | Davidson et al. | |
| 2004/0249291 A1* | 12/2004 | Honda et al. | 600/476 |
| 2006/0164511 A1* | 7/2006 | Krupnik | 348/65 |

FOREIGN PATENT DOCUMENTS

| | | |
|---|---|---|
| WO | WO 01/50180 | 7/2001 |
| WO | WO 01/50941 | 7/2001 |
| WO | WO 01/65995 | 9/2001 |
| WO | WO 02/054932 | 7/2002 |

OTHER PUBLICATIONS

U.S. Appl. No. 60/533,263, filed Dec. 31, 2003, Meron et al.

(Continued)

*Primary Examiner*—Brian L. Casler
*Assistant Examiner*—John F Ramirez
(74) *Attorney, Agent, or Firm*—Pearl Cohen Zedek Latzer, LLP

(57) ABSTRACT

A system and method may allow displaying a plurality of image streams, where the image streams may be divided, for example into a number of selected subset couplet images which follow predetermined criteria. According to some embodiments, each couplet may be displayed simultaneously or substantially simultaneously. A workstation may accept the images acquired by, for example a capsule and may display the images on a monitor as a moving image.

8 Claims, 8 Drawing Sheets

OTHER PUBLICATIONS

"Synchronized nQUAD Technology", www.cartesiantech.com.

Yang et al., "Two Image Photometric Stereo Method", SPIE, vol. 1826, Intelligent Robots and Computer Vision XI, 1992.

U.S. Appl. No. 10/364,508, filed Feb. 12, 2003, Davidson et al.

International Search Report, International Application No. PCT/IL03/00110. International Filing Date Feb. 12, 2003.

Cliff, Joseph: "Perfect motion on the Net", www.zdnet.co.uk/pcmag/trends/2001/04/06.html, printed Dec. 2001.

www.dynapel.com, Motion Perfect® product literature, printed Jul. 22, 2003.

Office Action from U.S. Appl. No. 10/364,508 dated Jun. 7, 2006.

* cited by examiner

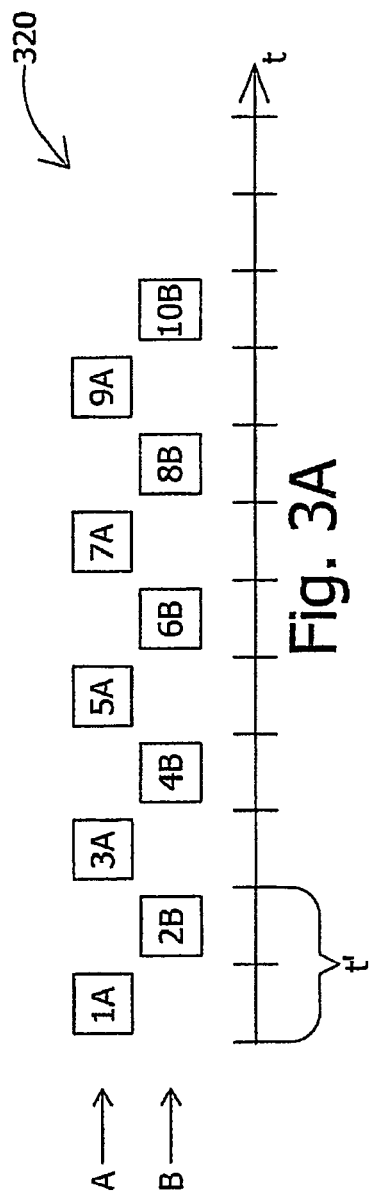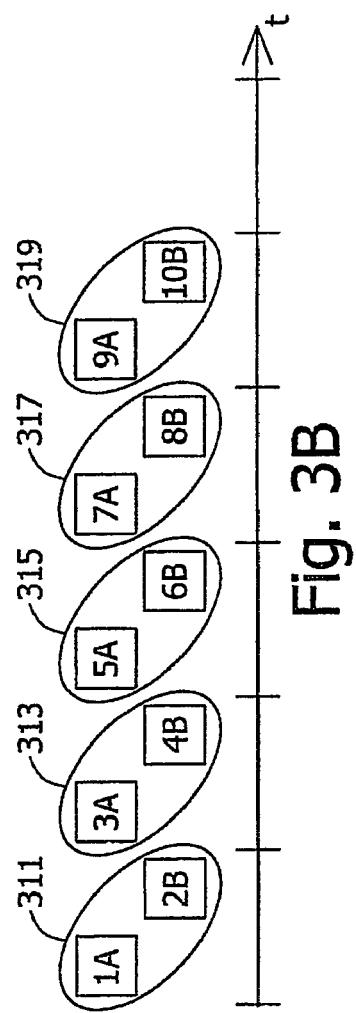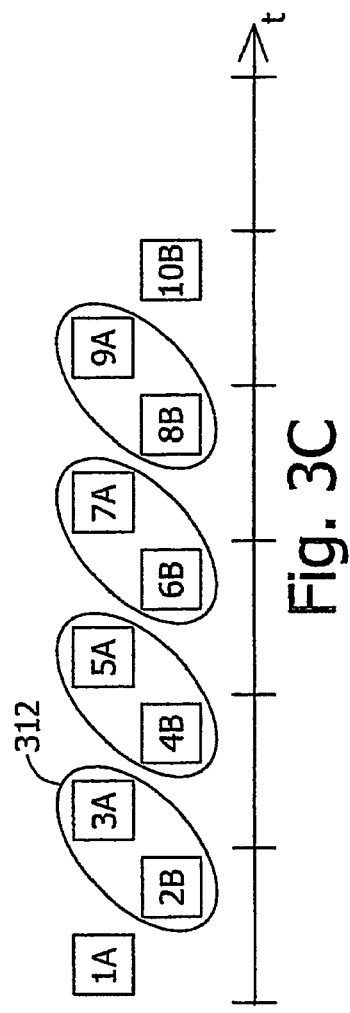

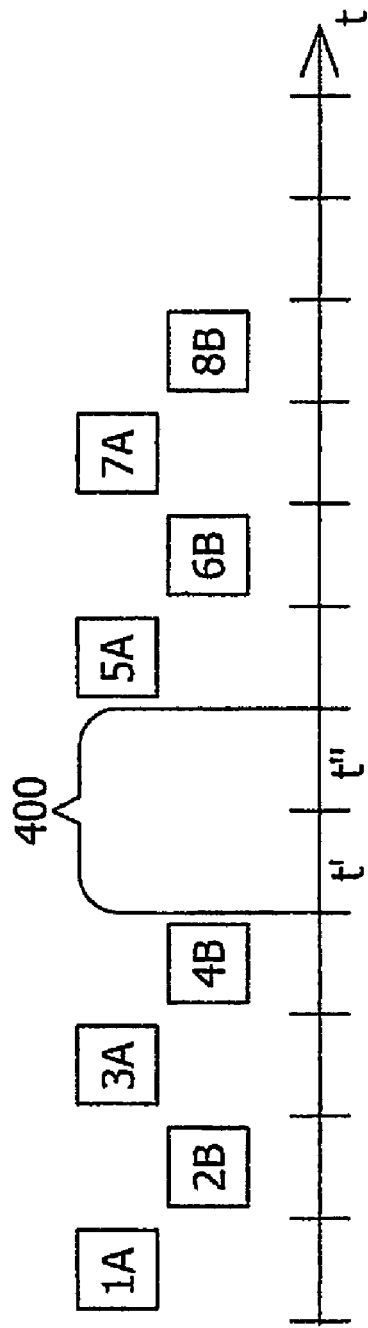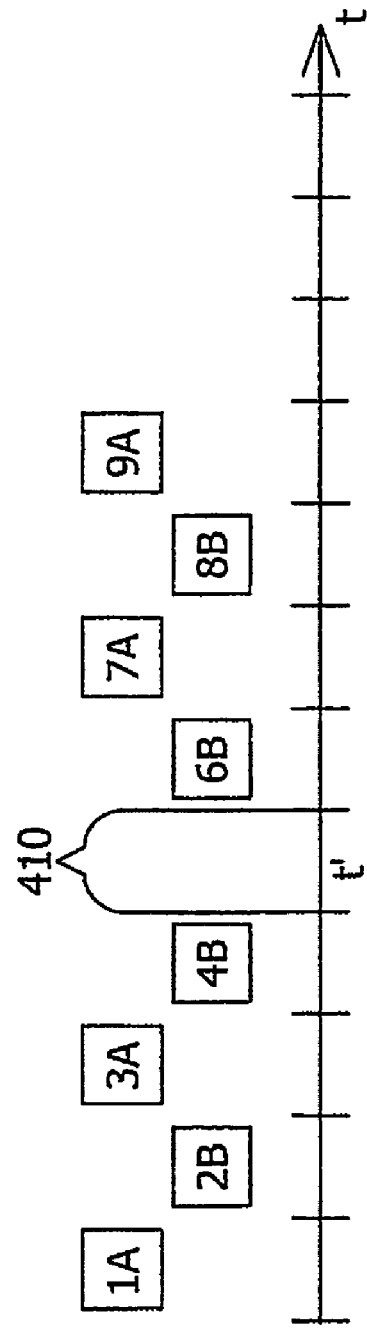

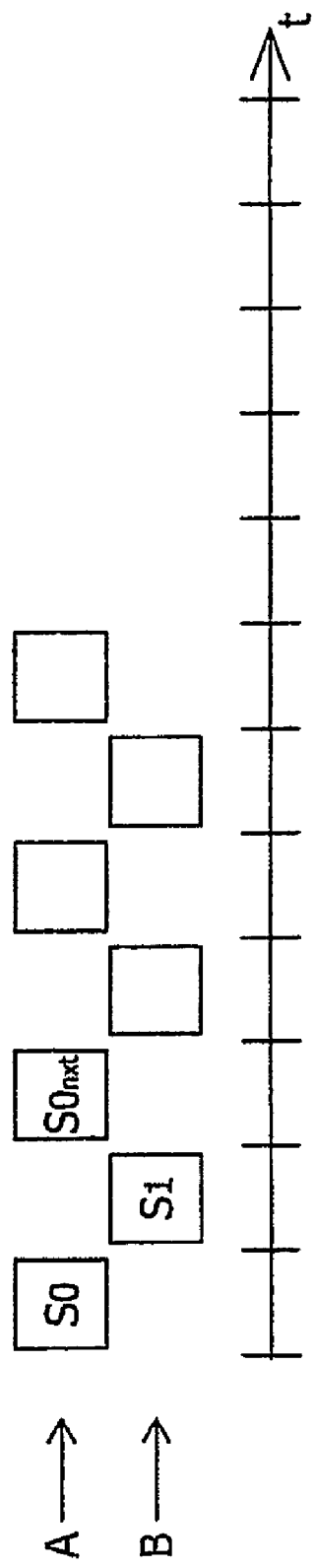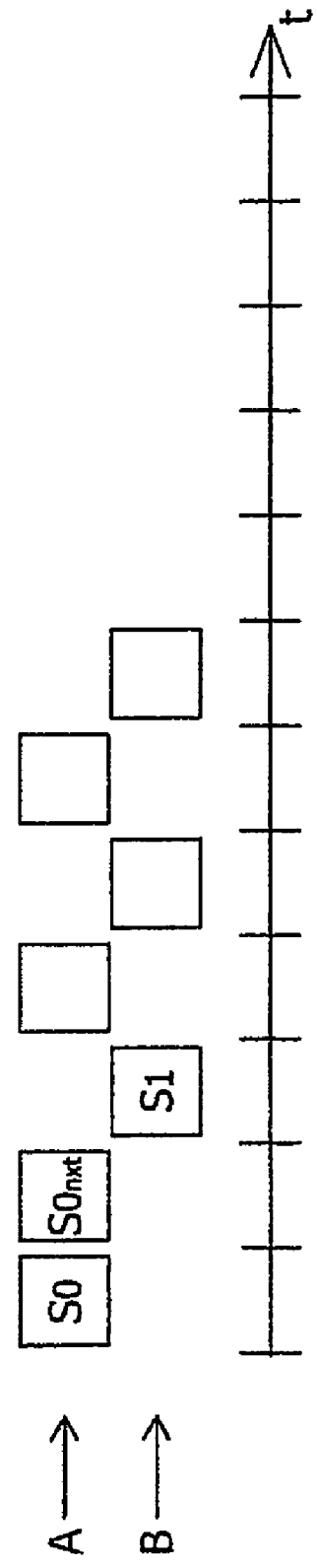

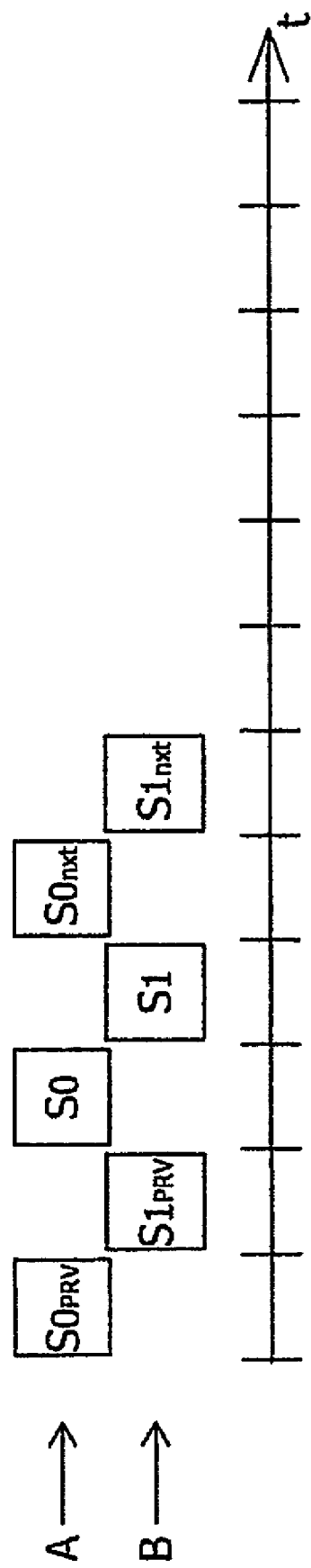

SYSTEM AND METHOD FOR DISPLAYING AN IMAGE STREAM

FIELD OF THE INVENTION

The present invention relates to a method and system for displaying and/or reviewing image streams. More specifically, the present invention relates to a method and system for effective displaying of an in vivo image stream.

BACKGROUND OF THE INVENTION

An image stream may be assembled from a series of still images and displayed to a user. The images may be created or collected from various sources for example, from an in-vivo system with a plurality of imagers According to one embodiment, each separated imager may capture images of a lumen such as the gastrointestinal (GI) tract and a transmitter may transmit the images to an external recording device while the capsule passes through the lumen. Large numbers of images may be collected by each imager for viewing and, for example, combined in sequence. An image stream of, for example, 40 minutes in length, containing for example about 4,800 frames, may be presented to the user for review. Other numbers of frames or lengths may be used.

According to some embodiments, one or several images may be absent from the image stream. This may be the result of one or more components within the in-vivo system, for example an imager which may be malfunctioning or which may not perform at a certain moment due to, for example the capsule angle and/or movement. In addition a malfunctioning could be the result, for example, of a recorder failing to record an image, or an unclear image rejected during a data screening and selection. Due to the missing images a gap may exist where for a certain amount of time no documentation is available and the resulting image stream may be inconsistent and/or incoherent.

Therefore, a need exists for a system and method that may serve as an accurate representation of the body parts that are being imaged.

SUMMARY OF THE INVENTION

An exemplary embodiment of the present invention provides a system and method for displaying a plurality of image streams, the image streams preferably being produced by an in vivo imaging device such as an ingestible capsule which may include more then one imager, for example, as was described in U.S. patent Ser. No. 10/046,541 to Meron et al., titled "SYSTEM AND METHOD FOR WIDE FIELD IMAGING OF BODY LUMENS" assigned to the common assignee of the present application and incorporated herein by reference. A workstation accepts images from each imager and may display the images as image streams, each image stream being displayed substantially simultaneously on a monitor which may include a plurality of image windows, a window for each image stream so that the image streams from the different imagers can be reviewed substantially simultaneously.

According to some embodiments, in cases where one image is rejected or skipped, a calculated break and skip process may occur in the stream in order to maintain synchronization of the image streams enabling the user to view the results in orderly and consistent fashion.

BRIEF DESCRIPTION OF THE DRAWINGS

The present invention will be understood and appreciated more fully from the following detailed description taken in conjunction with the drawings in which:

FIG. 3A is a schematic showing how a new image stream may be generated from two image streams, according to one embodiment of the present invention;

FIGS. 3B and 3C, depicts different methods for selecting groups of sequential images out of a number of image streams, according to embodiments of the present invention;

FIGS. 4A and 4B are schematic illustrations of two image streams with different types of gaps, according to embodiments of the present invention;

FIGS. 5A and 5B depict a method for synchronizing image streams of an in vivo imaging system, according to embodiments of the present invention;

FIG. 5C depicts a case where two images examined, do not meet the couplet requirements, according to embodiments of the present invention; and FIGS. 6A-B depict the stages following the selection of the first couplet for display, according to embodiments of the present invention.

DETAILED DESCRIPTION OF THE INVENTION

Figure 1:
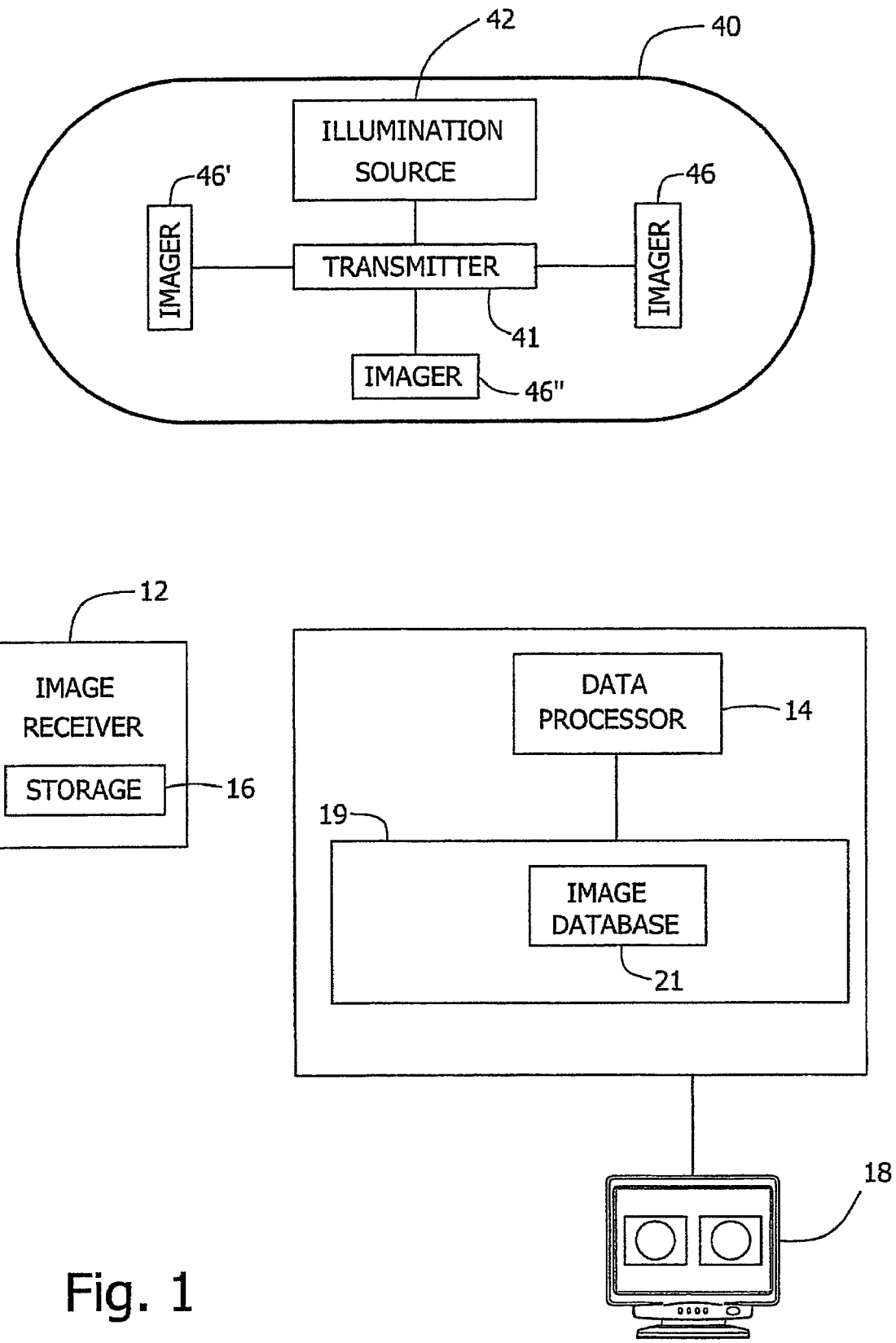
FIG. 1 shows a schematic diagram of an in-vivo imaging system according to one embodiment of the present invention.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. It will be appreciated that a variety of programming languages may be used to implement the teachings of the invention as described herein.

Some embodiments of the present invention are directed to a typically swallowable in-vivo device, such as an autonomous swallowable capsule. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in International Application WO 01/65995 and/or in U.S. Pat. No. 5,604,531, each of which are assigned to the common assignee of the present invention and each of which are hereby incorporated by reference. Of course, devices and systems as described herein may have other configurations and other sets of components.

Reference is made to FIG. 1, which shows a schematic diagram of an in vivo imaging system according to one embodiment of the present invention.

According to some embodiments of the present invention, the system may include an in-vivo device 40, for example a capsule.

Device 40 typically may be or may include an autonomous swallowable capsule, but device 40 may have other shapes and need not be swallowable or autonomous. Embodiments of device 40 are typically autonomous, and are typically self-contained. For example, device 40 may be a capsule or other unit where all the components are substantially contained within a container or shell, and where device 40 does not require any wires or cables to, for example, receive power or transmit information. According to one embodiment, device 40 may communicate with an external receiving and display system to provide display of data, control, or other functions. For example, power may be provided by an internal battery or a wireless receiving system. Other embodiments may have other configurations and capabilities. In an exemplary embodiment, the system may comprise a device 40 having a plurality of imagers 46, 46' and 46" for capturing images, an illumination source 42, for illuminating the body lumen, and a transmitter 41, for transmitting image and possibly other information to a receiving device. An optical system, including, for example, lenses or mirrors, may aid for example in focusing reflected light onto the imagers 46, 46' and 46".

According to some embodiments of the present invention transmitter 41 may includes control capability for, for example controlling the various operations of device 40, although control capability or one or more aspects of control may be included in a separate component. Transmitter 41 is typically an ASIC (application specific integrated circuit), but may be of other constructions; for example, transmitter 41 may be a processor executing instructions. Device 40 may include a processing unit separate from transmitter 41 that may, for example, contain or process instructions.

In one embodiment of the invention the system may include a single imager 46 and a single transmitter 41 and a plurality of optical paths. In this embodiment a plurality of narrow field images are obtained on the single imager and are then combined into a single image having a wider angle field than any of the narrow field images.

In another embodiment of the invention the system may include a plurality of imagers for example imagers 46, 46' and 46" and at least one transmitter 41 transmitting in a single channel of transmission or in multiple channels. In this embodiment the imagers may be positioned such that they capture images of different portions of the body lumen. A combined image of the images captured by the different imagers may show all the individually imaged portions, thereby covering a wide field.

In yet another embodiment of the invention the system may include a plurality of imagers for example imagers 46, 46' and 46", each having an optical path, wherein each imager and its optical path is partitioned off from its neighboring imagers. In this embodiment interference between imager operations is greatly reduced.

Preferably, located outside the patient's body in one or more locations, are an image receiver 12, preferably including an antenna or antenna array, an image receiver storage unit 16, a data processor 14, a data processor storage unit 19, and an image monitor 18, for displaying, inter alia, the images recorded by device 40. According to one embodiment, the image receiver 12 and image receiver storage unit 16 are small and portable, and are worn on the patient's body during recording of the images. According to embodiments of the present invention, data processor storage unit 19 includes an image database 21.

According to one embodiment of the present invention, data processor 14, data processor storage unit 19 and monitor 18 are part of a personal computer or workstation which includes standard components such as processor 14, a memory, a disk drive, and input-output devices, although alternate configurations are possible, and the system and method of the present invention may be implemented on various suitable computing systems.

Data processor 14 may include any standard data processor, such as a microprocessor, multiprocessor, accelerator board, or any other serial or parallel high performance data processor. Image monitor 18 may be a computer screen, a conventional video display, or any other device capable of providing image or other data Preferably, an imager, for example imager 46 is a suitable CMOS camera, such as a "camera on a chip" type CMOS imager specified by Given Imaging Ltd. of Israel and designed by Photobit Corporation of California, USA. In alternate embodiments, the imager 46 may be another device, for example, a CCD. The illumination source 42 may be, for example, one or more light emitting diodes, or another suitable light source.

In operation, imager 46 and/or imager 46' and/or imager 46" capture images and send data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 is sent to the data processor 14 or the data processor storage unit 19. For example, the image receiver storage unit 16 may be taken off the patient's body and connected to the personal computer or workstation which includes the data processor 14 and data processor storage unit 19 via a standard data link, e.g., a serial or parallel interface of known construction. The image data is then transferred from the image receiver storage unit 16 to the image database 21 within data processor storage unit 19. Data processor 14 may analyze and edit the data, and provide the analyzed data to the image monitor 18, where a health professional views the image data. Data processor 14 operates software which, in conjunction with basic operating software such as an operating system and device drivers, controls the operation of data processor 14. According to one embodiment, the software controlling data processor 14 includes code written in the C++ language and possibly additional languages, but may be implemented in a variety of known methods.

The image data collected and stored may be stored indefinitely, transferred to other locations, or manipulated or analyzed. A health professional may use the images to diagnose pathological conditions of for example the GI tract (e.g., the esophagus), and, in addition, the system may provide information about the location of these pathologies. While using a system where the data processor storage unit 19 first collects data and then transfers data to the data processor 14, the image data is not viewed in real time, other configurations allow for real time viewing.

The image monitor 18 presents the image data, preferably in the form of still and moving pictures, and in addition may present other information. According to one embodiment, the in-vivo device 40 may collect a series of still images as it traverses the GI tract. The images may be later presented as, for example, a stream of images or a moving image of the traverse of the GI tract. The in vivo imager system may collect a large volume of data, as device 40 may take several hours to traverse the GI tract, and may record images at a rate of, for example, two images every second, resulting in the recordation of thousands of images. The image recordation rate (or frame capture rate) may be varied.

Preferably, the image data recorded and transmitted by device 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel is recorded by a one byte (i.e., 0-255) brightness value. According to one embodiment, images are stored sequentially in data processor storage unit 19. The stored data may be comprised of one or more pixel properties, including color and brightness.

While, information gathering, storage and processing are performed by certain units, the system and method of the present invention may be practiced with alternate configurations. For example, the components gathering image information need not be contained in a capsule, but may be contained in any other vehicle suitable for imaging a lumen in a human body, such as an endoscope, stent, catheter, needle etc.

Preferably, data processor storage unit 19 stores a series of images recorded by device 40. The images device 40 records as it moves through a patient's GI tract may be combined consecutively to form a series of images displayable as an image stream. This moving image may be displayed in a window on monitor 18.

When viewing the image stream, the user is typically presented with one or more windows on monitor 18; in alternate embodiments multiple windows need not be used and only the image stream is displayed. In an embodiment where multiple windows are provided, for example, an image window may provide the image stream, or still portions of that image. Another window may include buttons or other controls that may alter the display of the image; for example, stop, play, pause, capture image, step, fast-forward, rewind, or other controls. Such controls may be activated by, for example, a pointing device such as a mouse or trackball. Typically, the image stream may be frozen to view one frame, speeded up, or reversed; sections may be skipped; or any other method for viewing an image may be applied to the image stream.

While the following discussion relates to the case where data from a device 40 is stored for later use, the system and method of the present invention may be used with systems allowing for real time viewing of image data.

In another embodiment, information gathering can be performed in another cavity besides a lumen in a human body. An example can include information gathered in an animal lumen. Another example can include information gathered from pipes or other cavities formed during a manufacturing process. Yet another example can be information gathered through a natural stream, for example, geological or marine formations.

Furthermore, while typically the components accepting, processing and displaying the image data are contained within a workstation system or PC, other systems may be used, and other (e.g., distributed) components may perform such image accepting, processing and displaying In one embodiment, the image stream may be presented to the viewer as multiple image streams in two or more windows, such that as the image streams are displayed a set of consecutive or "nearby" frames are displayed substantially simultaneously. For example, in one embodiment, two windows or viewing areas are displayed, each displaying one frame of an image stream. Typically, the frames are displayed substantially simultaneously.

In an exemplary embodiment, the windows or viewing areas are close together, with a minimum of blank or black space between the images, and typically horizontally and side by side, to allow a viewer to see the entirety of the images without substantially moving his eyes. The images may be distorted (e.g., displayed in a cone, oval or ellipse shaped field) to further reduce the space between them. The images may be displayed with symmetry. For example, the images may be displayed in the same horizontal plane.

Figure 2:
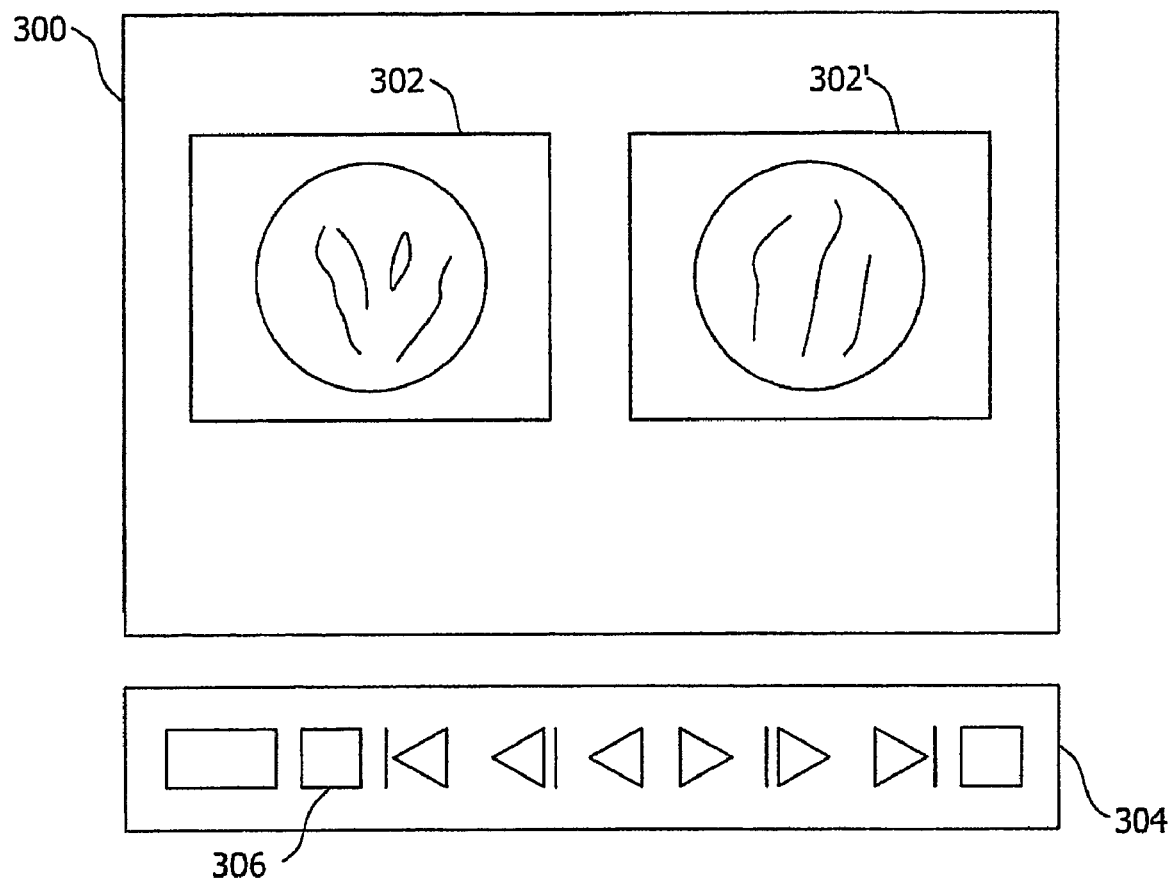
FIG. 2 depicts a portion of a display according to an embodiment of the present invention.

FIG. 2 depicts a portion of a display according to an embodiment of the present invention. Referring to FIG. 2, the display 300 is in multiple image stream mode. The display 300 may be displayed on, for example, image monitor 18. Typically, the display 300 includes a set of image windows 302 and 302', for displaying image streams, and a set of controls 304. The controls 304 may include, for example, a toggle control 306, allowing the user, for example to toggle between a multiple image stream mode and a single image stream mode. The controls 304 may also include, for example, conventional video controls, such as pause, stop, play, fast-forward, reverse, etc. In a typical embodiment, if the system is in a multiple image stream mode, the controls 304 may act on all image streams simultaneously; in alternate embodiments, other methods may be used, for example the controls 304 may act on a single image stream.

According to some embodiments of the present invention, the different image streams may be placed in different configurations on a viewing screen. For example, rather than horizontally, the image streams may be arranged vertically or diagonally.

In certain embodiments of the present invention, more than one image stream may be collected. For example, as show in FIG. 1 an in-vivo imaging device may include more than one imager (or one imager) collecting multiple image streams—possibly by including an imager or lens system in more than one location on the in-vivo imaging device. The imagers 46 may be arranged, for example, at either end of device 40, or at the same end of the device, in slightly different positions or different angles. Each imager, for example imager 46, may capture images and transmit the images via the transmitter 41 or via separate transmitters. Typically, each imager has associated an optical system. In such a case, an embodiment of the system and method of the present invention may display each image stream simultaneously, where each image displayed on the viewer screen was typically captured substantially simultaneously. In one embodiment, images from each of the imagers can be displayed substantially simultaneously so that image streams from different imagers can be reviewed simultaneously. For example, if three image streams from three different imagers are to be displayed substantially simultaneously on three image windows, the first and second frames of the first image stream may be displayed on the first image window, then the first and second frames of the second image stream may be displayed on the second image window and the first and second frames of the third image stream may be displayed on the third image window.

In another embodiment, image streams from each imager may be divided into a number of subset image streams and the subset image streams for one or more imagers may be shown substantially simultaneously. e.g., one subset image stream may include every other image frame whereas the second subset stream may include every other consecutive image frame (e.g. the first subset includes frames 1,3,5 etc and the second subset includes frames 2,4,6 etc.). Typically, in such a case images may be shown in matrix form so that each column may display frames from a single imager and each row may display frames from a different imager. Alternatively, each row may display frames from a single imager and each column may display frames from a different imager. In further embodiments, an image stream may be divided up or partitioned into sections, rather than based on substantially adjacent frames. For example, an image stream may be divided into a first section and a second section, where the first and second section are sequential. The two sections may be displayed simultaneously. More sections or partitions may be created.

Reference is now made to FIG. 3A, a schematic showing how a new image stream 320 may be generated from two image streams A and B and may be displayed substantially simultaneously, according to some embodiments of the present invention.

According to one embodiment of the present invention, an ID (Identification) number is assigned to each image, for example by a recorder during a recording process. Typically, a recorder receives the first image from image stream A and assigns to that image the ID number 1, and then records it. To simplify and further clarify this process the first image will hereafter be referred to as, for example image 1A, representing the first recorded image from an image stream A. In the next step the recorder receives the first image from image stream B and assigns to it the ID number 2B (e.g. second image received by the recorder and the first image from image stream B).

According to some embodiment of the present invention, image stream A (which includes images 1A, 3A, 5A, 7A, 9A etc.) represents for example all the images captured by a single imager, for example imager 46 which may be located at the front of the in vivo device, and image stream B (which includes images 2B, 4B, 6B, 8B, 10B etc.) represents all images captured from another imager, for example imager 46' located in the rear of the in vivo device. According to one embodiment, for example image window 302 (of FIG. 2) may display image stream A, while image window 302' may display image stream B so that as the two image streams A and B are displayed, a set of consecutive or "nearby" images are displayed.

According to one embodiment of the present invention, in each time slot, two images which may be consecutive are displayed, one in each window or viewing area, for example in time slot t' image 1A from image stream A may be displayed on image window 302, and image 2B from image stream B may be displayed, substantially simultaneously on image window 302'.

With reference to FIGS. 3B and 3C, different methods for selecting groups of sequential images out of an image stream are shown, for example selecting a plurality of sequential pairs out of two given streams, according to embodiments of the present invention.

FIG. 3B depicts a method for selecting sequential pairs, where the images are paired from image stream A and image stream B. According to one embodiment, the first image of each sequential pair 311, 313, 315, 317 and 319, will be lifted from stream A (and may be displayed for example in the left display window 302), while the second image of each pair may be lifted from image stream B (and may be displayed for example in the right display window 302'). For example, the first pair 311 is composed of images 1A and 2B, so that image 1A will be displayed in the left display window 302' and image 2B in the right display window 302' promptly. After pair 311 is displayed pair 313 will be chosen so that images 3A and 4B are displayed next, etc.

FIG. 3C depicts another exemplary method for selecting sequential pairs from image streams, for example out of two image streams A and B according to one embodiment of the present invention. As shown in FIG. 3C and according to one embodiment the method presented is based on selecting first an image from image stream B and consequently a sequential image from image stream A. For example pair 312 is composed of image 2B which will be displayed, for example in the left display window 302 and image 1A which will promptly appear in the right display window 302'. Other methods exist for selecting and displaying more then two images, lifted from more than two image streams.

FIGS. 4A and 4B depict different types of gaps which may occur during receiving and/or recording a plurality of images from an in vivo device, according to embodiments of the present invention. A gap may be defined as an image skip and/or a time period skip, during an image capture stage, for example when one or more imagers temporarily malfunctions, and/or during an image sorting and compilation stage where unclear or corrupt images are discarded. A gap may also be the result of a recording failure for example, in the image recorder device where the recorder does not record an image or does not assign one with the necessary ID number.

Reference is made to FIG. 4A, a schematic illustration of two image streams A and B with a gap 400 resulting for example from a recording failure in the image recorder, according to one embodiment of the present invention.

According to an embodiment of the present invention, when a gap occurs for example as a result of a recording failure, no ID number gap will be present since the entire time period unrecorded is skipped and the recorder, for example automatically assigns the next image recorded after the gap, an ID number subsequent to the last number assigned before the gap. For example, as shown in FIG. 4A, during time period t' no images from image stream A are recorded and afterwards, during time period t" no images from image stream B are recorded. As a result a gap 400 may occur where no images are recorded or displayed. When the next image for example from image stream A, is recorded after gap 400 it will be assigned as the ID number 5A, so that the images ID numbers are still in sequential order, while the chronological order is not maintained as images were lost during the time gaps. The significance of the gap created may appear on display. In this case while the time period for example, between images 3A and 4B is for example, ½ a second (the pre-set space between images captured) the time period between image 4B and 5A will be greater as a result of the time gap 400, despite the sequential ID numbers of the images.

FIG. 4B depicts a time gap 410 which results in an ID number gap and a time gap, according to one embodiment of the present invention. An ID number gap and a time gap may occur in cases where, for example, during the image compiling stage an image is determined corrupt or unclear according to a pre-set quality control standards. As a result the recorder will both skip the image and the ID number that should have been assigned to the unclear image. For example, if the image that should have been designated 5A, captured during time t' (right after image 4B) is corrupt, the recorder will skip that image, and the next image will be assigned an ID number 6B. A gap 410 will be present both in the image capture timeline and image ID numbers. As a result of the gap 410 the two streams A and B are no longer synchronized and the resulting stream displayed may not truly and dutifully reflect the actual in vivo body status.

Figure 5A:
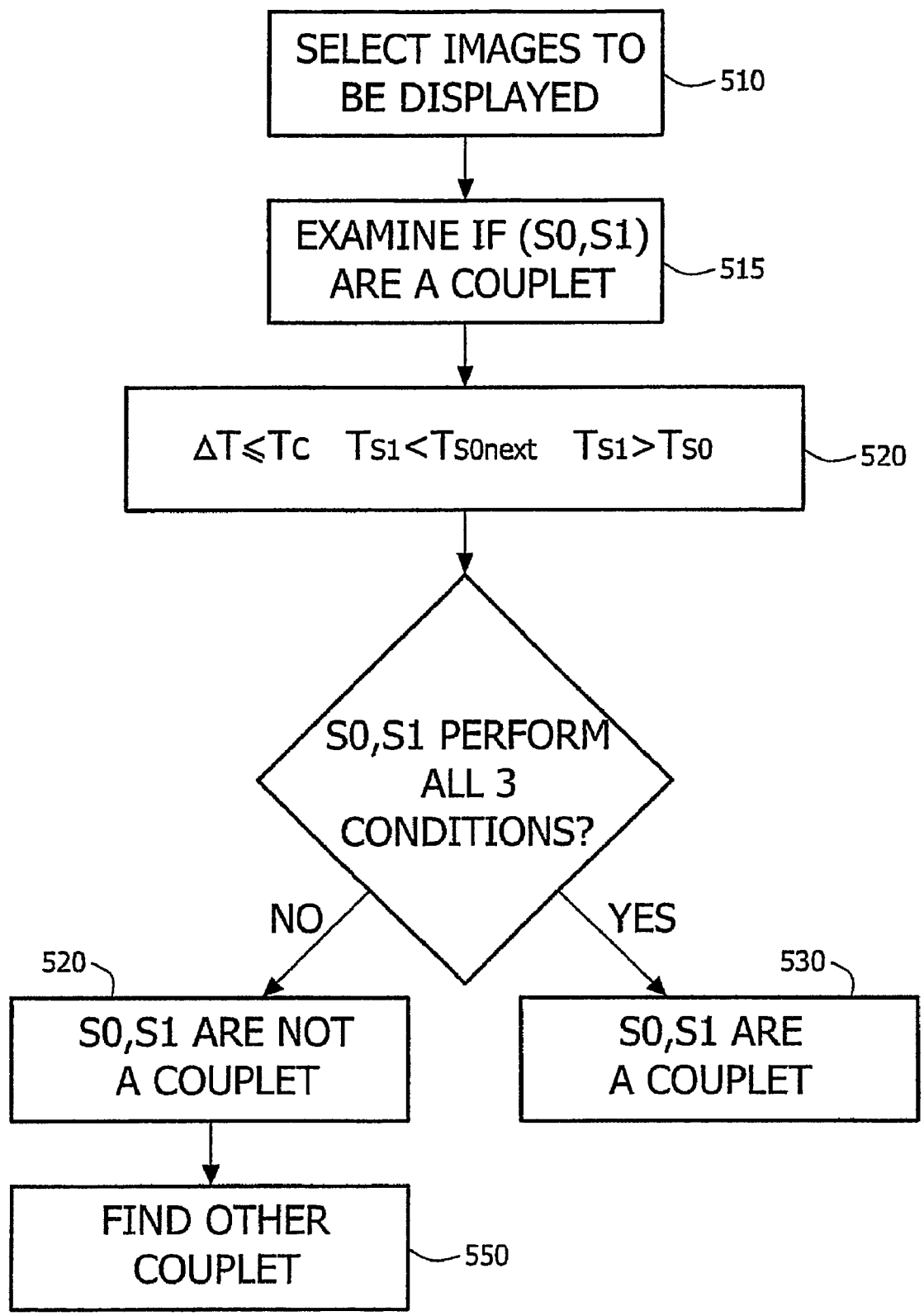

FIGS. 5A and 5B depict a method and/or a process for synchronizing image streams of an in vivo imaging system, according to embodiments of the present invention. FIG. 5A describes an exemplary algorithm that may be used in one embodiment of the invention. In step 510, the images to be displayed substantially simultaneously, for example the first two images, are selected based on, for example, a couplet algorithm as will be described hereinabove. This step may include selecting a number of images to be displayed substantially simultaneously from a stream of images when images are displayed chronologically, selecting the number of images from more than one stream of images, and/or selecting images from a stream or a subset stream of images. For example as shown in FIG. 5B three images are selected from two image streams A and B, e.g. image S0 and image S0next may be selected from image stream A while S1 may be selected from image stream B. According to one embodiment of the present invention, if image S0 is the first image captured by the in vivo device, S1 must be the next image captured in the time line from any other image stream. As shown in FIG. 5B, image S1 from image stream B is the closest in capture time line to image S0 from stream A as it was captured right after.

In step 515, two images, for example images S0 and S1 are examined to determine if they indeed form a solid pair e.g. a couplet. The determination of if two or more images should be displayed substantially simultaneously (e.g., if the two or more images form a pair) may be carried out by examining whether the two or more images meet a predetermined condition or set of conditions. According to some embodiments the condition(s) may be time related conditions. According to other embodiments other conditions may be used, such as conditions that relate to image properties and/or image quality (e.g., colors, brightness, etc.) According to one embodiment there are three underlying couplet factors (e.g. first chronological conditions) that contribute to the process of checking whether two images, for is example S0 and S1, form an image couplet (step 520). For example:

1. On one hand, S1 must be captured after S0;
2. On the other hand, S0next must be captured after S1; and
3. The image capture time difference between S0 capture time and S1 capture time is less or equal to a pre-set standard time constant Tc.

According to one embodiment of the invention the pre-set standard time constant Tc may be defined as a maximal time for a chronological condition(s), for example the first chronological conditions, to be valid.

According to one embodiment if the two images in question meet all three couplet conditions (step 530) they are declared a couplet and displayed as such, one after the other. If the two images S0 and S1 are a couplet the remaining images will be screened next to locate sequential pairs to display. If the pair in question (e.g. S0 and S1) do not meet the couplet conditions (step 540) new searches are perform (step 550) to locate a different couplet, where the new pair will be composed of S0 and the closest possible image in capture time line to S0.

FIG. 5C depicts a case where two images examined, do not meet the couplet requirements (of FIG. 5A). For example, S0 and S1 do not meet the second condition since S1 was captured after S0next, therefore they will not be declared a couplet.

Figure 6A:
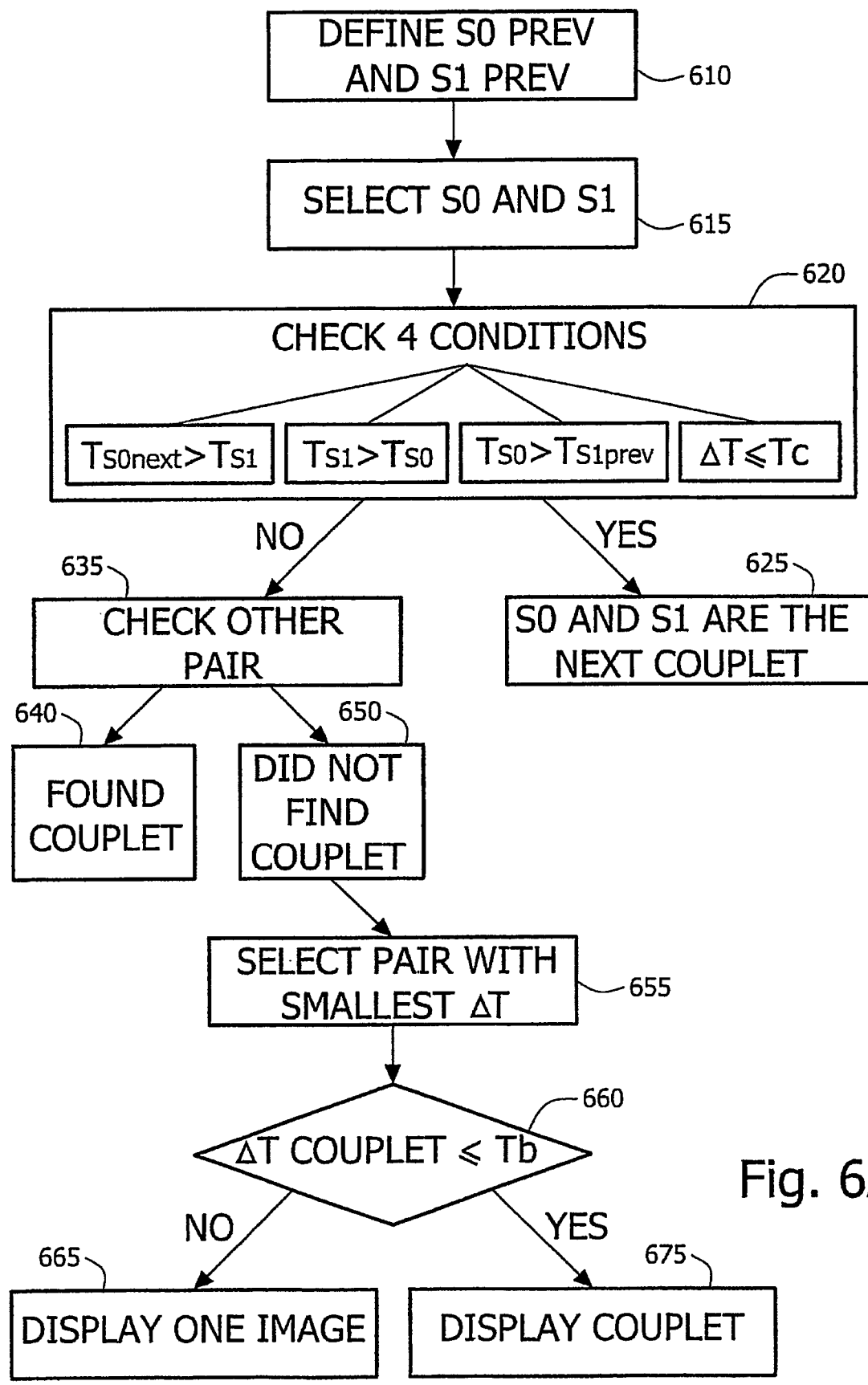

FIGS. 6A-B depict stages following the selection of the first pair for display, according to embodiments of the invention, for example as described in FIGS. 5A and 5B.

FIG. 6A is a flowchart depicting an algorithm for selecting the next sequential couplet from a plurality of image streams, according to one embodiment of the present invention. According to some embodiments of the present invention the algorithm shown in FIG. 6A may be used for selecting any couplet from a plurality of image streams. In step 610 the images in the previous selected couplet (e.g., S0 and S1 of FIG. 5A) are defined for example, as S0prev and S1prev. In stage 615 S0next and S1next are selected as the next possible couplet for inspection. For example, as shown in FIG. 6B image stream A includes images S0prev, S0 and S0next while stream B includes images S1prev, S1 and S1next. Thus, when the resulting stream is displayed, images S0prev and S1prev from image streams A and B may be displayed side by side. The next images S0 and S1 may be selected according to the herein above algorithm.

According to some embodiments of the present invention four conditions (e.g. next couplet chronological conditions) must be met (step 620) to ascertain images S0 and S1 indeed form the next sequential pair e.g. couplet 1. The time of capture for image S0next is later than the capture time for S1 (TS0next>TS1);
2. The time of capture for image S1 is later than the time of capture for image S0 (TS1>TS0);
3. The time of capture for image S0 is later than the time of capture for image S1prev (TS0>TS1prev); and
4. The image capture time difference between S0 capture time and S1 capture time is less or equal to a pre-set standard time constant Tc.

If the two images S0 and S1 meet these requirements they are determined to be the next couplet to be displayed (step 625). If the pair in question does not meet the requirements (step 635) new searches may be performed to locate a new pair, and several other options will be tested, such as pairing between S0 and S1prev, or another pair composed of S1 and S0prev.

If one of the pairs tested is found to meet the couplet requirements of step 620 it will be declared as the next couplet to be found (step 640). If none of the pairs tested meet the couplet requirements (step 650) the pair that will be chosen as the next couplet is the one maintaining the shortest possible time difference between image time capture (step 655) e.g.

the maximal time for a chronological condition(s), for example the second chronological conditions, to be valid. The best couplet will be displayed (step 675) if the image capture time difference between the images of the couplet is less or equal to a pre-set standard time constant Tb e.g. the minimal time period, for example an ID gap, which may be skipped (condition 660). If the couplet does not meet condition 660 only one image will be displayed (step 665). Thus, when all the couplets are found, the resulting stream may displayed, for example images S0prev and S1prev from the first couplet may be displayed side by side, then images S0 and S1, etc. The image streams are displayed on a display preferable substantially simultaneously, typically for observing and/or analyzing, for example, for detecting pathologies in the GI tract. In one embodiment of the invention, the main display engine is programmed to select the next two images to be displayed substantially at the same time (instead of the next image), and a display window displays those two images at the substantially the same time, until the next two images are selected from the display engine. In alternate embodiments other methods of combining images may be used. According to some embodiments images may be displayed as a moving image stream, such as a movie at a display rate of up to 30 frames per second. Other display rates are possible.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for synchronizing a display of in vivo images from at least two image streams captured by an in vivo imaging device, the method comprising:
    accepting sequentially numbered images acquired by an in-vivo device disposed within a GI tract, the images forming at least a first image stream obtained by a first imager and a second image stream obtained by a second imager;
    selecting a sequential image pair from the first and second image streams respectively, a first of said sequential pair being selected from the first image stream and a second of said sequential image pair being selected from the second image stream;
    if a difference in times of capture between the first image and the second image is less than or equal to a pre-set time constant, then displaying substantially simultaneously the sequential image pair; and
    if the difference in time of capture between the first image and the second image is greater than the pre-set time constant, then displaying only one image of said sequential image pair.

2. The method according to claim 1 comprising selecting an additional image from the first image stream, such that the first and additional images are in chronological order.

3. The method according to claim 1 comprising selecting at least two additional sequential images from said first and second image streams, respectively; if a difference in time of capture between the first additional image and the second additional image is less than or equal to said pre-set time constant, then displaying substantially simultaneously the additional sequential image pair; and if the difference in times of capture between the first additional image and the second additional image is greater than the pre-set time constant, then displaying only one image of said additional sequential image pair.

4. The method according to claim 1 wherein said in-vivo device is an autonomous in vivo imaging device.

5. A system for displaying in synchronization at least two in vivo image streams captured by an in vivo imaging device, the system comprising:
    an image storage configured to accept sequentially numbered images acquired by an in-vivo device disposed within a GI tract, the images forming at least a first image stream obtained by a first imager and a second image stream obtained by a second imager, and to store the in vivo images;
    a processor programmed to select a sequential image pair, a first image selected from the first image stream and a second image selected from the second image stream sequential to said first image; and
    a display configured to display at least one image, wherein said processor is to provide to said display for substantially simultaneous display the first image from the first image stream and the second image from the second image stream if a difference between times of capture of the first image from the first image stream and the second image from the second image stream is less than or equal to a pre-set time constant, and wherein said processor is to provide to said display only one image of said first and second images if the difference in times of capture between the first image and the second image is greater than the pre-set time constant.

6. The system according to claim 5 wherein the in vivo images are images transmitted from an autonomous in vivo imaging device.

7. The system according to claim 5 wherein the display comprises a plurality of image windows, each image window displaying an image stream.

8. A method for selecting in vivo images from an image stream, the method comprising:
    accepting sequentially numbered images acquired by an in-vivo device disposed within a body lumen, the images forming at least a first image stream obtained by a first imager and a second image stream obtained by a second imager;
    selecting first and second consecutive images from the first image stream and an image from the second image stream;
    displaying substantially simultaneously the first image from the first image stream and the image from the second image stream if a capture time difference between the first image from the first image stream and the image from the second image stream is less or equal to a pre-set standard time constant; and
    displaying a single image if a difference in times of capture between the first image from the first image stream and the image from the second image stream is larger than the pre-set time constant.

* * * * *